United States Patent
Bhat et al.

(10) Patent No.: US 6,645,195 B1
(45) Date of Patent: Nov. 11, 2003

(54) INTRAVENTRICULARLY GUIDED AGENT DELIVERY SYSTEM AND METHOD OF USE

(75) Inventors: Vinayak Dinesh Bhat, Sunnyvale, CA (US); Jeffrey A. Steward, Lakewood, CO (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/755,462

(22) Filed: Jan. 5, 2001

(51) Int. Cl.[7] .............................................. A61M 25/01
(52) U.S. Cl. ........................ 604/528; 604/523; 604/532
(58) Field of Search ................................. 604/528, 523, 604/507, 508, 509, 532, 533

(56) References Cited

U.S. PATENT DOCUMENTS

| | | | |
|---|---|---|---|
| 5,366,490 A | * | 11/1994 | Edwards et al. |
| 5,464,395 A | * | 11/1995 | Faxon et al. |
| 5,499,630 A | * | 3/1996 | Hiki et al. |
| 5,704,361 A | * | 1/1998 | Seward et al. |
| 6,159,225 A | * | 12/2000 | Makower |
| 6,190,353 B1 | * | 2/2001 | Makower et al. |
| 6,302,875 B1 | * | 10/2001 | Makower et al. ........... 604/528 |
| 6,390,973 B1 | * | 5/2002 | Ouchi |

* cited by examiner

*Primary Examiner*—Michael Mar
*Assistant Examiner*—Khoa Huynh
(74) *Attorney, Agent, or Firm*—Squire, Sanders & Dempsey, L.L.P.

(57) ABSTRACT

The invention relates to an apparatus and method for locating and positioning a medical device in a patient. The catheter based drug delivery device uses ultrasound imaging technology to facilitate tracking of the catheter as it is maneuvered through the body of a patient. The device includes a secondary body portion and a main body portion that are in signal communication with each other. Ultrasound signals generated from and received by the device are transmitted to an intravascular ultrasound (IVUS) system. An image of the structures surrounding and including the device is displayed on the IVUS system. A drug delivery needle, housed within the main body portion, can be precisely positioned at the target site using the ultrasound signals. This allows accurate delivery of drug to the target site and, thus, enhanced treatment capabilities.

7 Claims, 8 Drawing Sheets

INTRAVENTRICULARLY GUIDED AGENT DELIVERY SYSTEM AND METHOD OF USE

FIELD OF THE INVENTION

The present invention relates to an apparatus and method for locating and positioning a medical device in a patient's body. In particular, the present invention relates to a catheter based drug delivery device having ultrasound imaging technology that facilitates tracking of the catheter as it is maneuvered through the body of a patient.

BACKGROUND

The number and variety of medical device and methods available to repair the effects of cardiovascular disease has increased rapidly over the last several years. More particularly, alternatives to open heart surgery and cardiovascular by-pass surgery have been extensively investigated, resulting in non-surgical procedures such as Percutaneous Transluminal Coronary Angioplasty (PTCA), Percutaneous TransMyocardial Revascularization (PTMR) and gene therapy. These procedures are primarily directed toward the reduction of stenosis within the vasculature of a patient or the generation of new blood vessels in the body for restoring blood flow to tissues after injury or trauma.

In general, PTCA is a catheter-based technique whereby a balloon catheter is inserted into the blocked or narrowed coronary lumen of a patient. Once the balloon is positioned at the target site, the balloon is inflated causing dilation of the lumen. The catheter is then removed from the target site thereby allowing blood to freely flow through the unrestricted lumen.

Although PTCA procedures aid in alleviating intraluminal constrictions, such constrictions or blockages reoccur in many cases. The cause of these recurring obstructions, termed restenosis, is due to the body responding to the trauma of the surgical procedure. As a result, drug therapies are often applied in combination with the PTCA procedure to avoid or mitigate the effects of restenosis at the surgical site. The drugs are delivered to the site via a needle housed within the catheter. The term "drug(s)," as used herein, refers to all therapeutic agents, diagnostic agents/reagents, genetic materials, growth factors, angiogcnic substances and other similar chemical/biological agents or fluids, including combinations thereof used to treat and/or diagnose restenosis, thrombosis, angiogenesis and related conditions.

Other procedures, such as those developed to control the effects and occurrence of angiogenesis, also utilize a catheter for delivering drugs to diseased vessels and ischemic myocardium. Angiogenesis is a process whereby new blood vessels are grown in the body for healing wounds and for restoring blood flow to tissues after injury or trauma. Angiogenesis occurs naturally in the body, both in health and in disease states. For example, in females, angiogenesis occurs during the monthly reproductive cycle to rebuild the uterus lining and to mature the egg during ovulation. In addition, angiogenic growth factors are also present during pregnancy to build the placenta and create the vessels necessary for circulation between the mother and fetus.

Angiogenesis also occurs in various disease states, such as cancer, diabetic blindness, age-related macular degeneration, rheumatoid arthritis, coronary artery disease, stroke, and other disorders. In cases of excessive angiogenesis, the new blood vessels feed diseased tissues, destroy normal tissues and, with respect to cancer, allow tumor cells to escape into the circulation and lodge in other organs. Conversely, insufficient angiogenesis causes inadequate blood vessel growth thereby impeding circulation which, in turn, potentially leads to tissue death.

Although angiogenesis occurs naturally in the body, various procedures have been developed to artificially control the occurrence and effects of angiogenesis. One such procedure is Percutaneous TransMyocardial Revascularization (PTMR). PTMR utilizes a laser catheter to create small channels in the diseased tissue. The channels re-establish direct blood flow to the tissue and allow oxygen-rich blood to saturate the oxygen-starved tissue. PTMR is generally used for the treatment of severe, end-stage coronary disease.

Another catheter-based procedure used to promote angiogenesis involves gene therapy. For this procedure, genetic material is delivered directly to the diseased area of the body via a catheter. In particular, genetic material, such as Vascular Endothelial Growth Factor (VEGF), is incorporated into gene delivery vehicles called vectors, which encapsulate therapeutic genes for delivery to the diseased cells. Many of the vectors currently in use are based on attenuated or modified versions of viruses. The vectors may also be synthetic versions in which complexes of DNA, proteins, or lipids are fonned into particles capable of efficiently transferring genetic material. A needle injection catheter is used to deliver the vectors containing the genetic material to the appropriate cells of the patient in a safe and efficient manner.

PTCA and angiogenic procedures are generally performed by inserting a guiding catheter into the artery of the patient and advancing the distal end of the catheter to the target area. Once the catheter is positioned at the target area, fluids are then delivered to the target site, i.e. diseased tissue. The term "fluid(s)," as used herein, refers to all drugs, genetic materials, growth factors, angiogenic substances, therapeutic agents/substances, diagnostic agents/reagents and other similar chemical/biological agents, including combinations thereof, used to treat and/or diagnose restenosis, thrombosis, angiogenesis and related conditions.

The above-described devices and methods for treatment of cardiovascular disease, and other similar diseases and conditions not specifically described, offer many advantages to potential users. However, it has been discovered that such devices and methods may be deficient in their current fluid-delivery characteristics. A potential drawback is the inability to deliver fluid directly to the target site due to the plaque or diseased tissue barrier in the artery. Although the venous coronary system has been proposed as one of the routes for local fluid delivery to the ischemic myocardium and diseased arterial walls, blood flow direction presents a challenge. Since the direction of blood flow in the venous system is opposite to that in the arterial system, the use of contrast medium does not help to navigate the vasculature as it does so on the arterial side. Further, the location of the venous system also presents an obstacle to accurately positioning the delivery device close to the targeted arterial site.

SUMMARY

In view of the above, it is apparent that there is a need to provide a fluid delivery device offering improved fluid delivery features. There is also a need to provide a method of using such an improved fluid delivery device that is convenient, efficient and cost effective. It is also desirable that the catheter-based fluid delivery device be used in combination with intravascular ultrasound (IVUS) technology for accurately mapping the location and distance of various structures in the body of the patient.

In accordance with various aspects of the present invention, an apparatus or device is capable of delivering a drug directly to a target site comprising a main body portion and a secondary body portion. Housed within the elongated, tubular main body portion, having a distal end and a proximal end, are a retractable ultrasound component, a guide wire lumen, one or more fluid lumen and a balloon. The retractable ultrasound component has a transducer located near the distal end of the main body portion. The guide wire lumen is configured to slidably receive a primary-guide wire therein. Further, the balloon is attached near the distal end of the main body portion and is in fluid communication with the fluid lumen. The flexible, secondary body portion of the drug delivery device has a secondary-guide wire having a proximal end and an ultrasonic opaque component located at a distal end of the secondary-guide wire. The secondary-guide wire is in signal communication with the retractable ultrasound component of the main body portion.

The invention also relates to a method of positioning a drug delivery device near a target site. The method includes an act of providing a drug delivery device having a secondary guide wire and a main body portion. The secondary guide wire is inserted into a first lumen of a patient and guided to a target area. An ultrasonic opaque portion, located at the distal end of the secondary guide wire, is positioned near the target site. The main body portion of the device is inserted into a second lumen of a patient or adjacent to the secondary guide wire. A real time image generated from ultrasound signals from the secondary body portion and the main body portion are processed and displayed on an IVUS system. Using these signals, the main body portion is navigated to a location in the target area nearest the ultrasonic opaque portion. The main body is then positioned at a site in the second lumen closest to the target site in the first lumen using the ultrasound signals.

In an alternate embodiment, the method further includes delivering a drug directly to a target site. In this embodiment, the main body portion includes a retractable needle. Once the device is located near the target site, as previously described, the retractable needle is extended from the main body portion so that the needle penetrates the target site. The drug is then dispensed directly into the target site using the retractable needle. The method allows needle position to be precisely determined, both in relationship to the device as well as the target site for drug delivery. This allows accurate delivery of drug to the target site and, thus, enhanced treatment capabilities.

BRIEF DESCRIPTION OF THE DRAWINGS

The features of the described embodiments are specifically set forth in the appended claims. However, embodiments relating to both structure and method of operation are best understood by referring to the following description and accompanying drawings, in which similar parts are identified by like reference numerals.

FIG. 2b is a detailed sectional view of the distal portion of the main body portion of the device of FIG. 2a;

DETAILED DESCRIPTION

Figure 1:
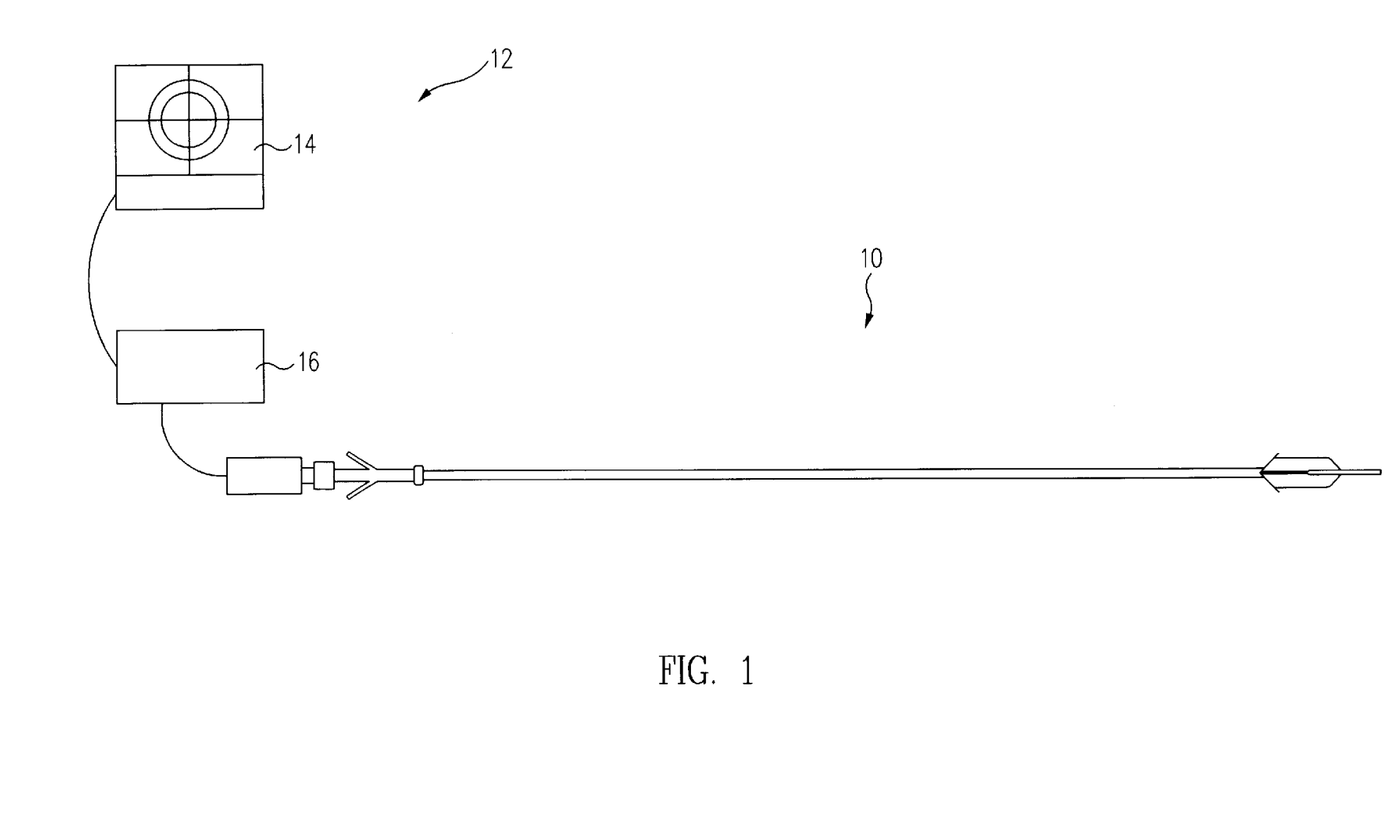
FIG. 1 is a perspective view of a catheter based drug delivery device and ultrasound imaging system.

An example of a catheter-based drug delivery device 10 and ultrasonic imaging display system 12 are shown schematically in FIG. 1. The imaging display system 12 includes an image processor having a display 14 and a signal processor 16. Both the image processor 14 and signal processor 16 can include general purpose processors of the type that are commonly used in connection with various medical, analytical or diagnostic devices. Additional disclosure of the ultrasonic imaging system 12 is discussed in further detail below.

Figure 2A:
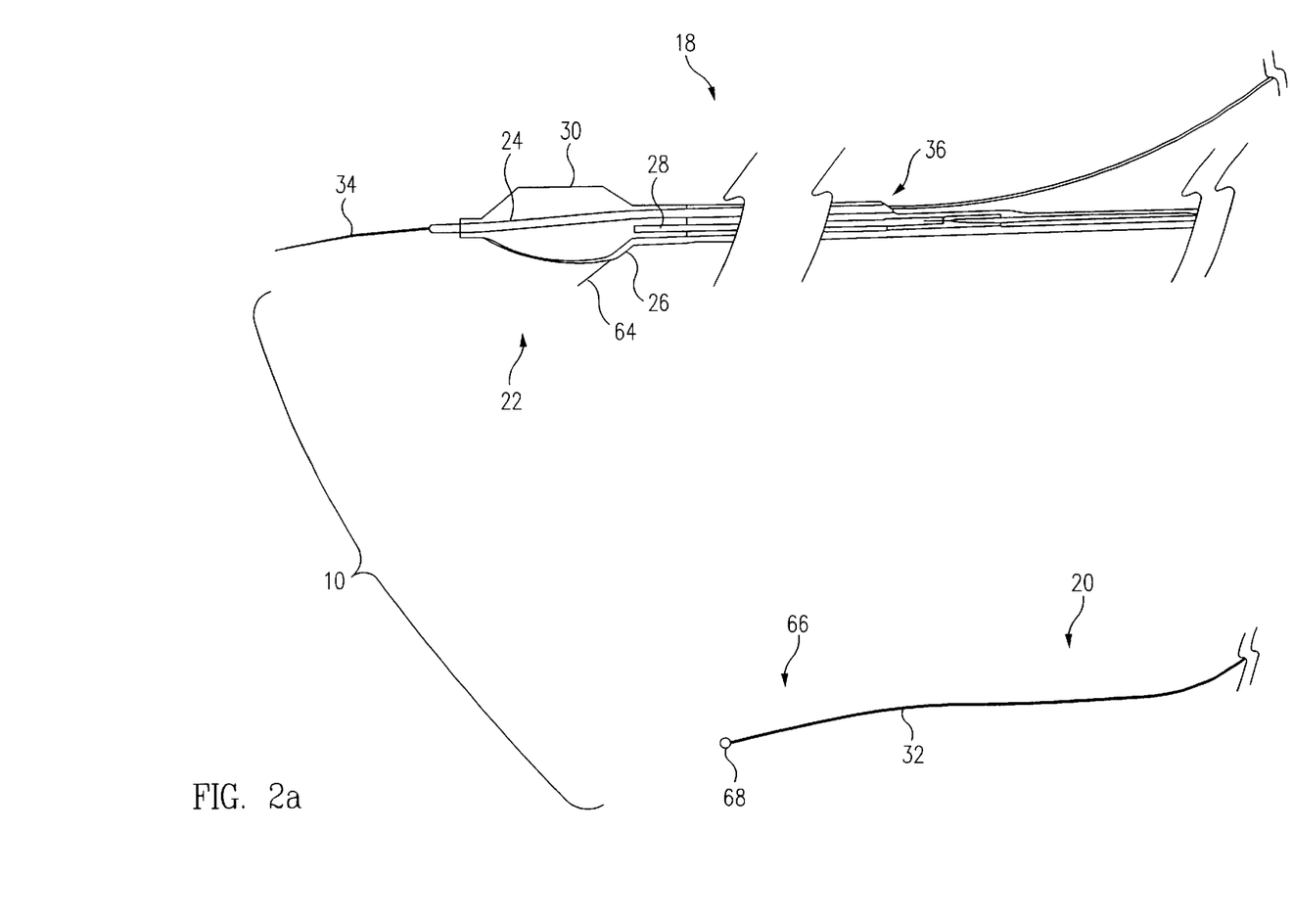
FIG. 2a is a sectional view of one embodiment of a catheter based drug delivery device.

FIG. 2a shows a cross-sectional view of the catheter-based drug delivery device 10. In general, the device 10 includes an elongated, tubular main body portion 18 and a flexible, secondary body portion 20. The main body portion 18 has a distal end 22 and a proximal end (not shown). Housed within the main body portion 18 is, in general, an ultrasound component (not shown), a guide wire lumen 24, a needle lumen 26, one or more fluid lumen 28 and an inflatable balloon 30. The secondary body portion 20 includes a secondary guide wire 32, further described below. The drug delivery device 10 is configured so that the secondary guide wire 32 and ultrasound component of the main body portion 18 are in signal communication. In the spirit of convenience and brevity, the device 10 referenced in the text and figures of the present disclosure is configured according to the above-described design. However, it should be noted that other designs of the cathcter-based needle drug delivery device are also within the scope of the claimed invention.

The structure of the inflatable balloon 30 is similar to those well known in the art. The inflatable balloon 30 may be used for various procedures including, but not limited to, opening narrowed passageways, distributing drugs to specific target sites, and delivering/positioning stents or other medical devices within the lumen. The term "target site," as used herein, refers to sites/tissue areas both inside and outside the vessel/lumen. The inflatable balloon 30 is located at the distal end 22 of the device 10 and is initially deployed in a low profile, deflated condition. When the balloon 30 is positioned at the target site it is inflated with fluid via an inflation port (not shown) located near the proximal end of the device 10. During inflation of the balloon 30, fluid flows from the inflation port, through the fluid lumen 28, and to the balloon 30. In addition, the fluid flows through the same lumen 28, but in the opposite direction, upon deflation and subsequent removal of the balloon 30.

Figure 2B:
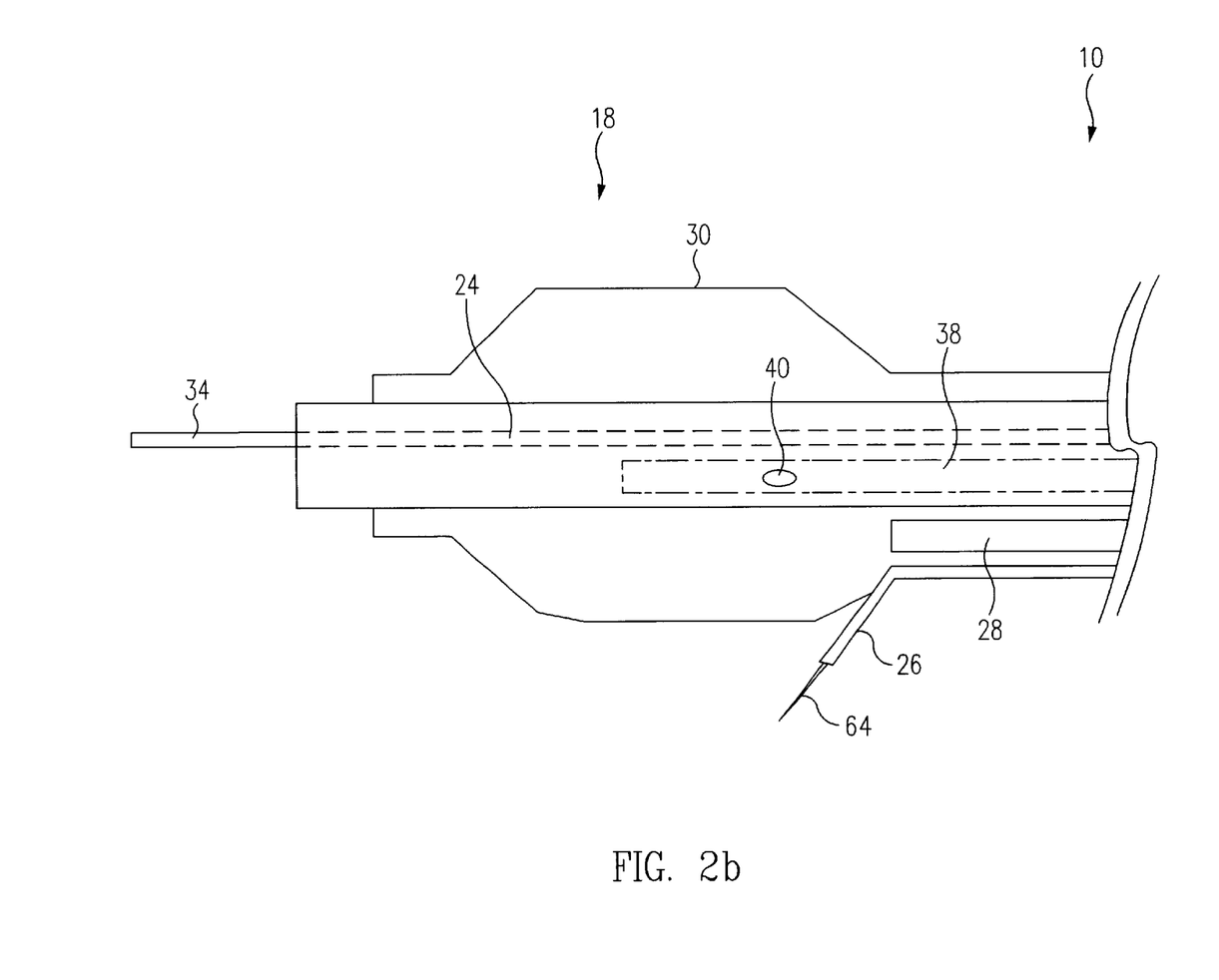

As shown in FIG. 2b, extending partially along the length of the device 10 is the guide wire lumen 24 and ultrasonic element lumen 34. The guide wire lumen 24 provides a passageway for a movable guide wire 34. The guide wire 34 extends from beyond the distal end 22 of the device 10 to a guide wire exit 36 shown in FIG. 2a located near the proximal end of the device 10. The guide wire serves as the steering mechanism of the device 10 and enables an operator to maneuver the device 10 through the various vessels and lumens of the patient to the chosen target site. In one embodiment, overall length and diameter of the guide wire 34 are within the range of approximately 74.8 inch to 118.1 inch (190 cm to 300 cm) and 0.0152 inch to 0.019 inch (0.0386 cm to 0.0483 cm), respectively. The guide wire may be fabricated from a variety of materials including, but not limited to, stainless steel, Nitinol™, platinum and polymers. These and other similar materials exhibit the required structural properties, such as strength and flexibility, desired in guide wire elements.

Figure 3:
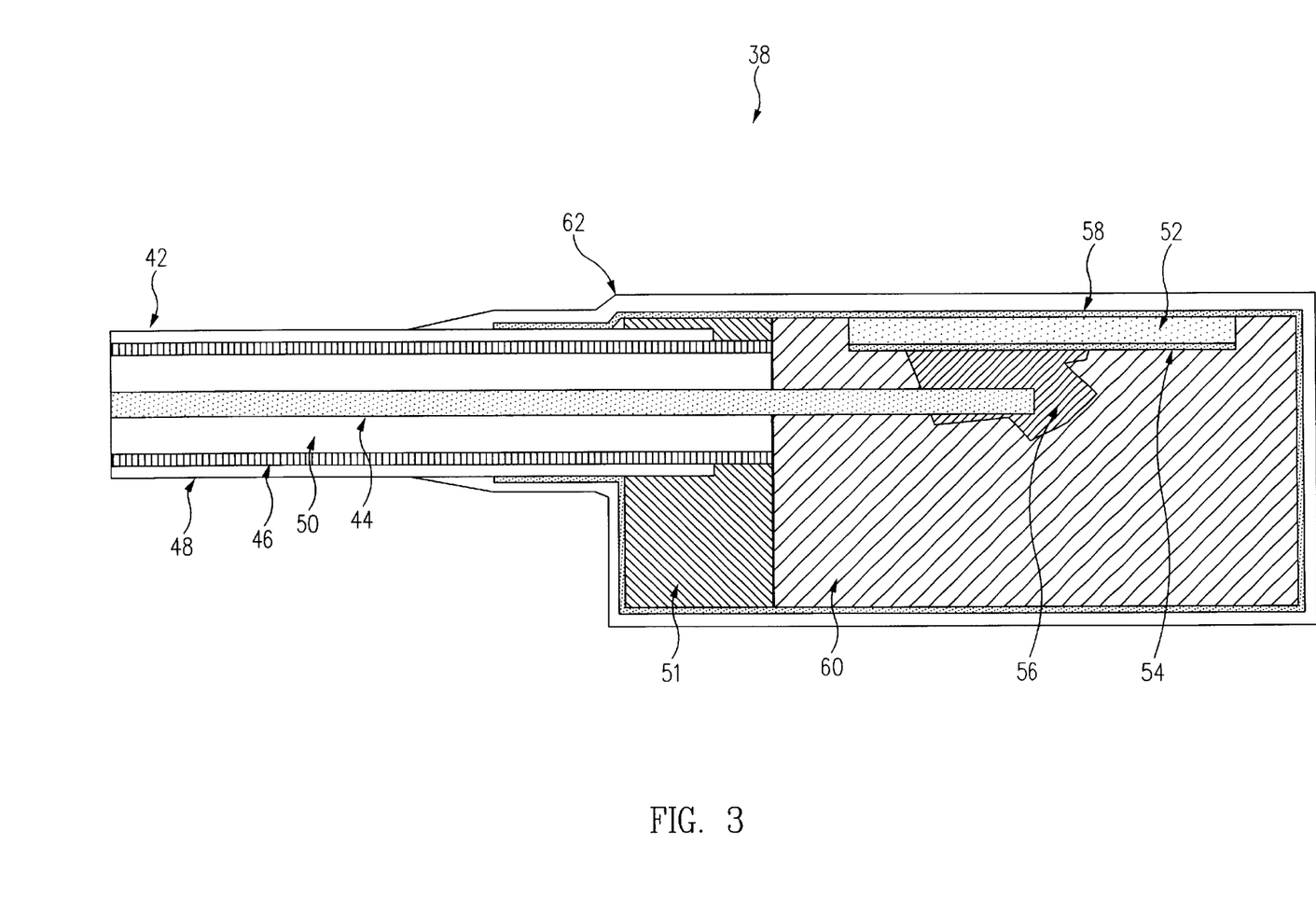
FIG. 3 is a perspective view detailed cross-sectional view of the ultrasound transducer of FIG. 2b.

A lumen houses the retractable ultrasonic element 38 of the device 10. As shown in FIGS. 2b and 3, the distal end of the ultrasonic clement 38 comprises an ultrasound transducer or transducer array 40 and the proximal end contains the associated co-axial cable that connects to the imaging display system 12, i.e. IVUS imaging system (not shown). In general, ultrasonic waves generated by the ultrasonic element 38 impinge on the surface of the target area. The timing/intensity of the ultrasonic waves reflected back to the transducer 40 differentiates between the various anatomic boundaries or structures of the target area. The waves detected by the transducer 40 are converted to electric signals that travel along the coaxial cable 42 to the imaging system 12. The electrical signals are processed and eventually arranged as vectors comprising digitized data. Each vector represents the ultrasonic response of a different angular sector of the target area and/or bodily lumen. As such, the amplitude of the reflected ultrasonic waves/electric signals is displayed as variable shades of, for example, gray on the display. Thus, anatomic structures with different acoustic density are portrayed with varying degrees of brightness, resulting in a visible, displayed image of the various structures within the body.

The coaxial cable 42 of the ultrasonic element 38 contains an insulated solid or stranded center conductor 44 (e.g., a wire) surrounded by a solid or braided metallic shield 46, wrapped in a plastic cover or jacket 48. The wire 44 is the primary conductor, whereas the shield 46 is used for ground potential. The insulation 50 surrounding the wire 44 is typically made of a dielectric material, such as polyester or plastisol, and functions to sustain the current traveling within the wire 44 with minimal dispersion. A conductive material 51, for example copper, gold, palladium, conductive epoxy or other similar materials, is used to attach and electrically connect the distal end of the coaxial cable 42 to the ultrasound transducer 40.

The ultrasound transducer 40 has a piezoelectric crystal 52 configured for optimal acoustic output efficiency and energy conversion. In a preferred embodiment, the crystal 52 is made of PZT or lead ceramic materials, such as $PbTiO_3$ (lead titanate) or $PbZrO_3$ (lead zirconate). As shown in FIG. 3, the back surface 54 of the piezoelectric crystal 52 is coated with conductive material plating such as gold, platinum, palladium and other similar conductive materials. The gold plating provides a sufficient electrical contact to the back 54 of the piezoelectric crystal 52 to connect with the wire 44 of the coaxial cable 42. A conductive epoxy 56 is used to mechanically and electrically attach or connect the coaxial center conductor 44 to the back 54 of the piezoelectric crystal 52. In addition to conductive epoxy 56, solder joints, cold solders, ultrasonic velds and other similar attachment techniques can also be used.

The front surface 58 of the piezoelectric crystal 52 is also coated with conductive material plating. The front surface plating electrically connects the front surface 58 of the crystal 52 to the coaxial shield 46 through the conductive material 51. Partially surrounding the crystal 52 and its related components is a backing material 60. The backing material 60 serves as a nonconductive sound absorbing material that eliminates sound waves coming off the back 54 of the piezoelectric crystal 52. In addition, the backing material 60 also facilitates rapid reduction in piezoelectric oscillations.

To electrically isolate the ultrasound transducer 40, the transducer 40 is covered in a paralyene coating 62. The paralyene coating 62 is a quarter wave-matching layer that does not interfere with the acoustic output or response of the piezoelectric element 52. In addition, the paralyene electrically isolates the two sides of the piezoelectric crystal 52 and associated electrical connections.

As shown in FIGS. 2a and 2b, the device also includes a retractable needle 64 housed in the needle lumen 26 and freely movable therein. The hollow, tubular shaped needle 64, having an inner diameter of approximately 0.002 inch to 0.010 inch ($5.1 \times 10^{-3}$ cm to $25.4 \times 10^{-3}$ cm) and an outer diameter within the range of approximately 0.004 inch to 0.012 inch ($10.2 \times 10^{-3}$ cm to $30.5 \times 10^{-3}$ cm), provides a fluid conduit that extends from the proximal end to the distal end of the needle 64. The distal end of the needle 64 terminates in a curved, tissue-piercing tip having an angle of curvature between 30 degrees to 90 degrees. Needle curvature facilitates placement of the needle tip near to or within the desired target tissue. Further, to allow easy needle deployment from and retractability into the lumen, yet provide sufficient structural strength for insertion into tissue, the needle 64 is preferably fabricated from, for example, stainless steel, NiTi (nickel titanium), platinum or other similar semi-rigid materials. The needle 64 can also be coated with fluoroscopically opaque materials to enhance its imaging capabilities on the fluoroscope.

The needle 64 is used to deliver drugs, therapeutic agents, diagnostic substances, genetic material, growth factors, angiogenic substances and other fluids not specifically described herein to the target site. The fluids are dispensed from the distal tip of the needle 64. In an alternate embodiment, the needle 64 can also be used to aspirate fluid from tissue.

The flexible, secondary body portion 20 comprises a movable, secondary guide wire 32 having a proximal end (not shown) and a distal end 66. An ultrasound opaque end 68, configured, for example, as a hollow sphere, is located near the distal end 66 of the secondary body portion 20. The secondary body portion 20 can be maneuvered through the various vessels and lumens of the patient to the chosen target site. Overall length and diameter of the secondary body portion 20 are within the range of approximately 135 cm to 300 cm (53.15 inches to 118.11 inches). In general, the ultrasound opaque end 68, when configured as a hollow sphere. has a diameter within the range of approximately 0.1 mm to 1.0 mm ($3.94 \times 10^{-3}$ inch to $3.94 \times 10^{-2}$ inch). The secondary body portion 20 may be fabricated from a variety of materials including, but not limited to, stainless steel, Nitinol™, platinum and polymers. The ultrasound opaque end 68 can be made from magnetic materials, ultrasound sensors, electrical sensors or other similar materials/components not specifically described herein.

In an alternate embodiment, the secondary body portion 20 includes an ultrasonic component or element (not shown) similar in structure and function to the ultrasonic element 38 of the main body portion 18. Both the main body portion 18 and secondary body portion 20 are in signal communication with each other to synchronize and coordinate the body portions 18,20 relative to one another and, further, provide the device 10 with imaging and mapping capabilities. Examples of such capabilities include, but are not limited to, calculating distances and structural sizes, determining locations of device components and internal structures, and controlling depth of needle penetration.

Method of Use

The retractable ultrasonic element 38 of the drug delivery device 10 allows the various structures located at a target area within a patient's lumen to be imaged and mapped using conventional IVUS technology. The mapped images are used to accurately determine and control the location of the device 10 within the lumen relative to the target area and/or target site. Generally, the target area and/or target site is located at or near the narrowed or diseased portion of the lumen requiring drug therapy. As such, during a coronary procedure, for example, the secondary body portion 20 is taken down the coronary artery and positioned along the occlusion. The main body portion 18 is introduced in the ventricle or venous system, depending on the procedure and desired results. An ultrasound signal from the secondary body portion 20 is used to position the distal end 22 of the main body portion 18, using the retractable ultrasonic element 38, at a site in the ventricle or venous system (i.e. the delivery site) closest to the occlusion in the arterial system. Therefore, the drug delivery device 10 allows accurate positioning of the device 10 nearest the target site and, together with an IVUS system, can be used to calculate the distance between the delivery site and the occlusion. Once the drug delivery device 10 is properly positioned within lumen, additional ultrasonic images can be generated and used to control the depth of penetration of the retractable needle.

During use of the device 10, the distal end 66 of the secondary body portion 20 is introduced into the lumen of the patient and guided to the target area via conventional methods. The main body portion 18 is then inserted into a lumen of the patient and maneuvered adjacent to the target area and secondary body portion 20 via conventional methods or ultrasonic imaging techniques. In one embodiment, the target area is the area in the patient's lumen that is partially or completely occluded due to plaque buildup. In another embodiment, shown in FIG. 4, the target area 70 is the diseased tissue area or ischemic myocardium. As such, the main body portion 18 can be introduced in the patient's ventricle 72 or the patient's venous system through the coronary sinus accessed from the jugular vein. In the spirit of convenience and brevity, the target area 70 referenced in the text and figures of the following disclosure is the diseased or ischemic myocardium. Further, the drug delivery route is via the ventricle 72. However, it should be noted that other target areas and drug delivery routes are also within the scope of the claimed invention.

Figure 4:
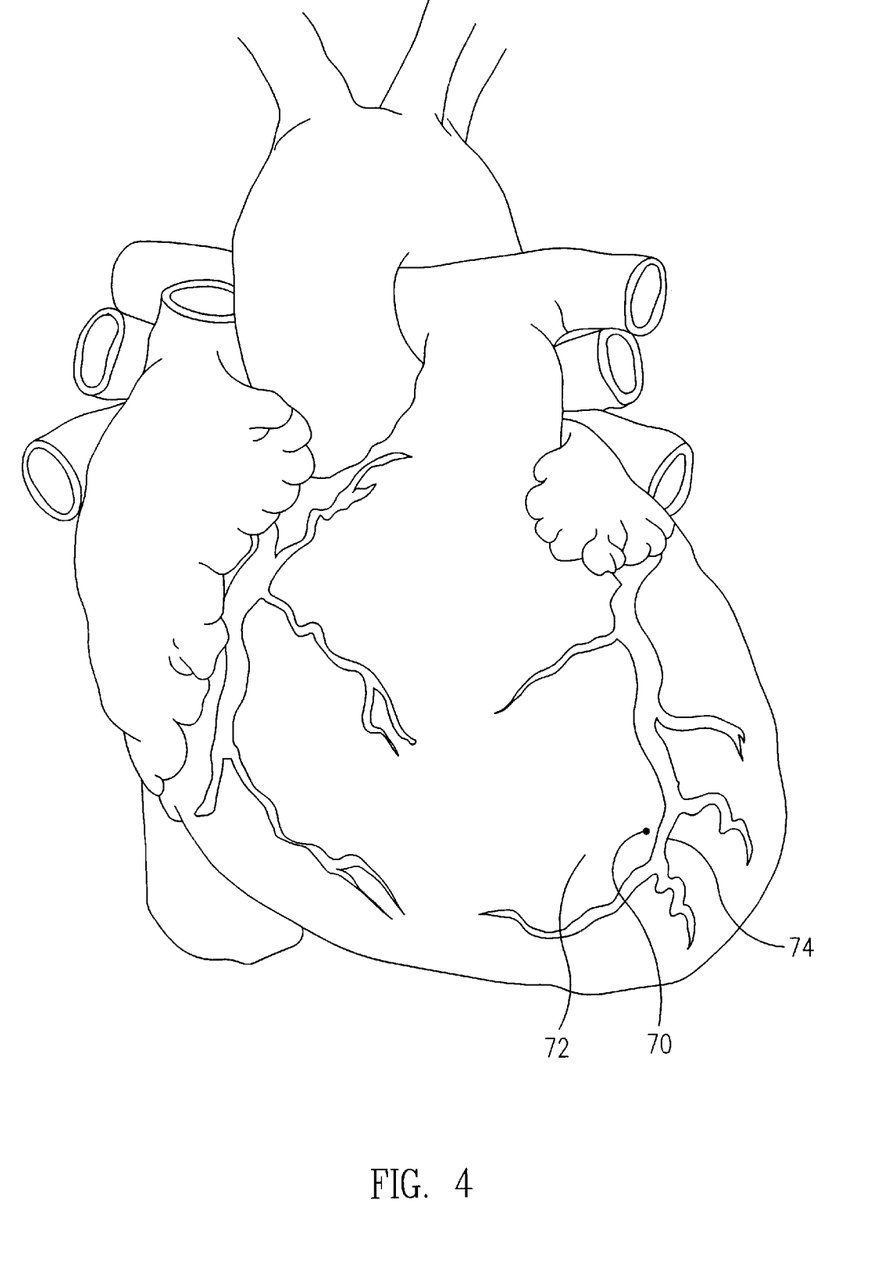
FIG. 4 illustrates one embodiment of a target area for the drug delivery device.
Figure 5:
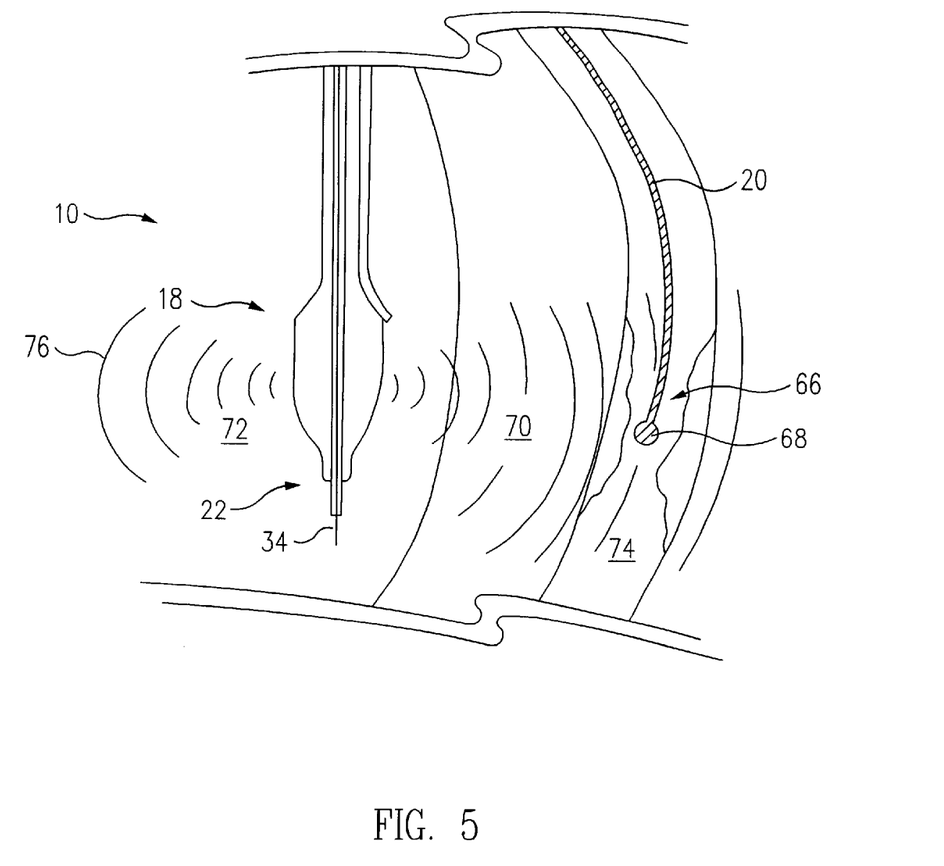
FIG. 5 illustrates a sectional view of a lumen.

In general, the device 10 is introduced into an artery or vein in the arm or leg of the patient (not shown). As shown in FIGS. 4 and 5, the distal end 66 of the secondary body portion 20, in particular the opaque hollow sphere 68, is positioned in the diseased or narrowed coronary artery 74 adjacent the target area 70 utilizing conventional fluoroscopic imaging methods. The main body portion 18 is maneuvered into the patient's lumen, for example the ventricle 72, via an artery or vein in the arm or leg of the patient (not shown). In one embodiment, the ultrasonic element 38 or the main body portion 18 and hollow sphere 68 of the secondary body portion 20 are positioned in two distinct lumens separated by tissue. During, for example, a drug delivery procedure, the drug is injected into the tissue located between the two lumens. In another embodiment, the guide wire 34 of the main body portion 18 together with fluoroscopic imaging techniques are used to generally position the distal end 22 of the main body portion 18 near the target area 70. In an alternate embodiment, the ultrasound transducer 40 (not shown) of the retractable ultrasonic element 38 (not shown), located at the distal end 22 of the main body portion 18, is used together with an IVUS system to position the distal end 22 of the main body portion 18 near the target area 70.

The target area 70, including the secondary body portion 20 and sections of the ventricle 72 and coronary artery 74, is then imaged using IVUS technology. In general, a signal, in the form of a voltage pulse, generated by the signal processor of the IVUS system (not shown) travels through the coaxial cable 42 to the ultrasound transducer 40 of the ultrasonic element 38. The voltage pulse results in an electromotive force that causes the crystal 52 of the transducer 40 to oscillate, thereby producing sonic waves.

As shown in FIG. 5, the ultrasonic waves 76, forming an energy waveform field, emanate from the ultrasound transducer (not shown) and are transmitted into the surrounding tissues and structures. Waves 76 reflected by tissues, the hollow sphere 68 of the secondary body portion 20 and other structures near the transducer and detected/received by the ultrasound transducer are converted back to electric signals. The differential density between, for example, the hollow sphere 68 and the target tissue results in discrete and easily identifiable IVUS signals. The signals travel along the coaxial cable to the imaging system where they are then processed. As a result, a first axial, sectional image of the various structures is generated and displayed on the IVUS system. The image that appears on the display is then adjusted and optimized, in terms of gain, zoom, and other related resolution variables.

Figure 6:
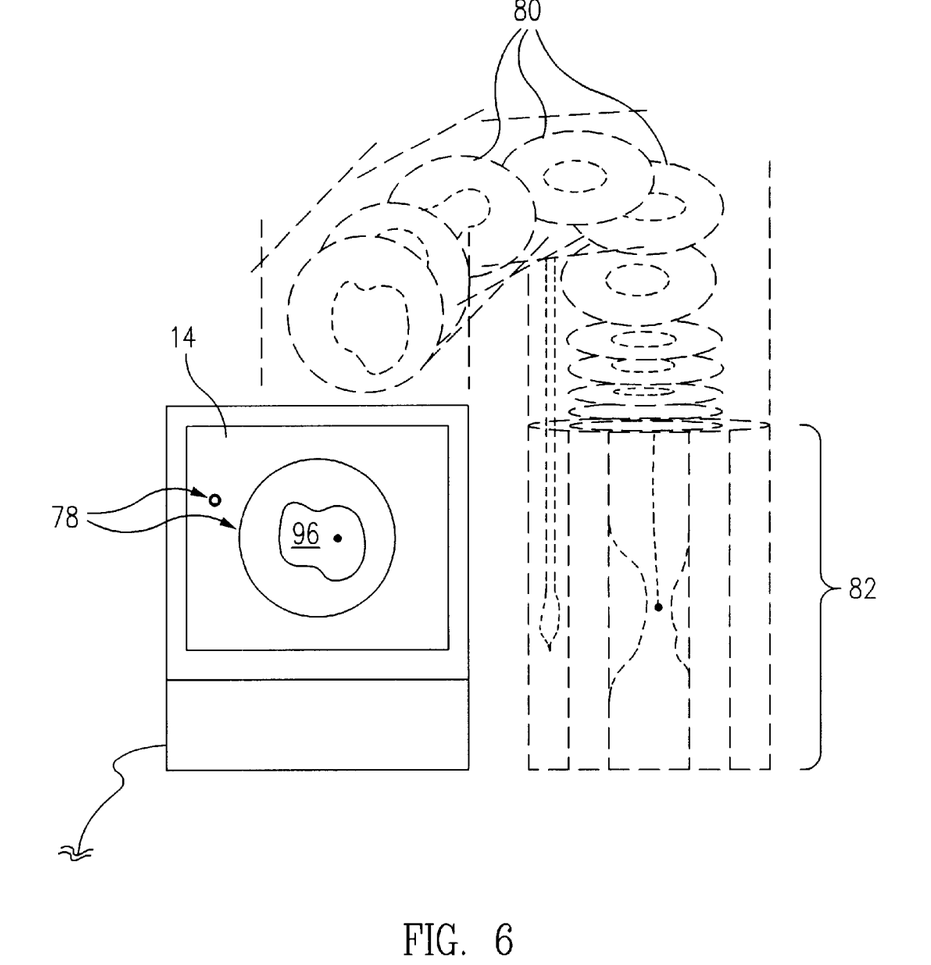
FIG. 6 illustrates one embodiment of the display, imaging and stacking functions of an IVUS system.

To obtain a mapped, longitudinal view of the surrounding tissues and structures, the distal end of the ultrasound transducer is slowly moved in the proximal direction. Transducer movement may be either manually and/or automatically controlled. Approximately hundreds of sectional images are generated, similar to the above-described single, sectional image procedure, and then stacked in real time. FIG. 6 representatively illustrates the imaging and stacking functions performed by an IVUS system. A single, sectional image of the structures 78 is displayed on the monitor 14. Additional sectional images, generated as the transducer is slowly moved through the lumen, are shown in hatched lines 80. These images are collected and processed, or stacked, by the system in real-time mode. The developing longitudinal view of the lumen and structures (also shown in hatched lines 82) as the transducer is moved through the lumen can also be displayed on the monitor of the IVUS system. Therefore, the IVUS system can either display a two-dimensional cross-sectional image or a three-dimensional longitudinal view of the lumen and structures.

In an alternate embodiment, the internal lumen and associated structures may also be imaged by initially positioning the tip of the ultrasonic element proximal to the target area. As such, a longitudinal view of the lumen and structures may be obtained by slowly pushing the ultrasonic element in the distal direction until the tip of the ultrasonic element is located distal to the target area. In another embodiment, the ultrasonic element is pushed and/or pulled repeatedly across the target area to obtain numerous detailed images and views of the lumen and associated structures.

In addition to displaying the internal lumen, target area and associated structures, the device 10 is also used to accurately track and determine the position and location of various structures with respect to the target site 70. Further, the device 10 can also be used to accurately calculate distances between the various structures. For example, the following distances can be calculated using the disclosed device: distance between the hollow sphere 68 of the secondary body portion 20 and the tip of the needle 64; distance from the needle tip to the target site 70; distance of needle extension from the catheter 10; etc.

Figure 7:
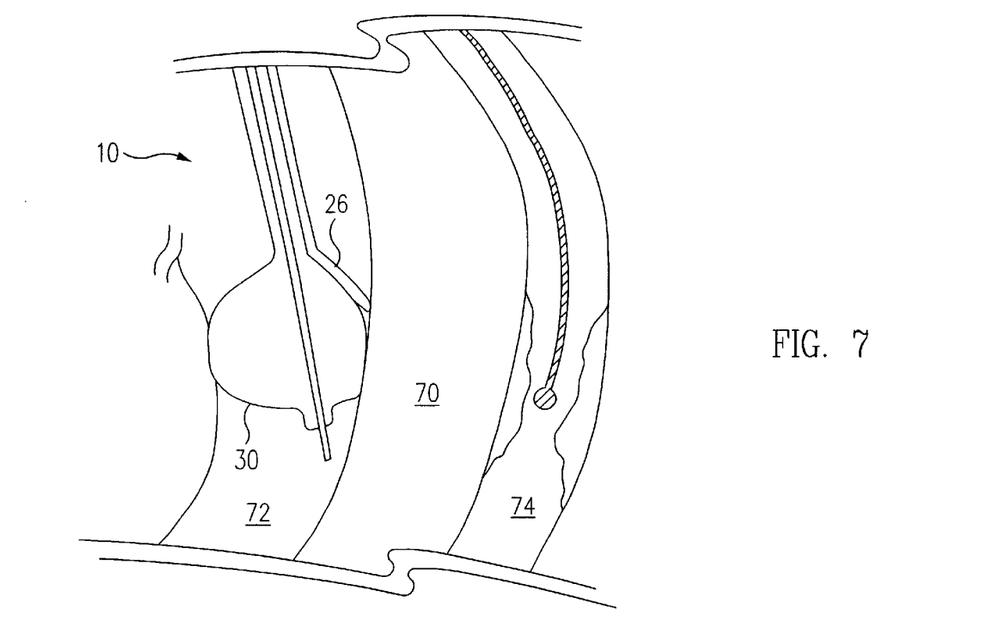
FIG. 7 illustrates one embodiment of the image of the lumen and device of FIG. 4.
Figure 8:
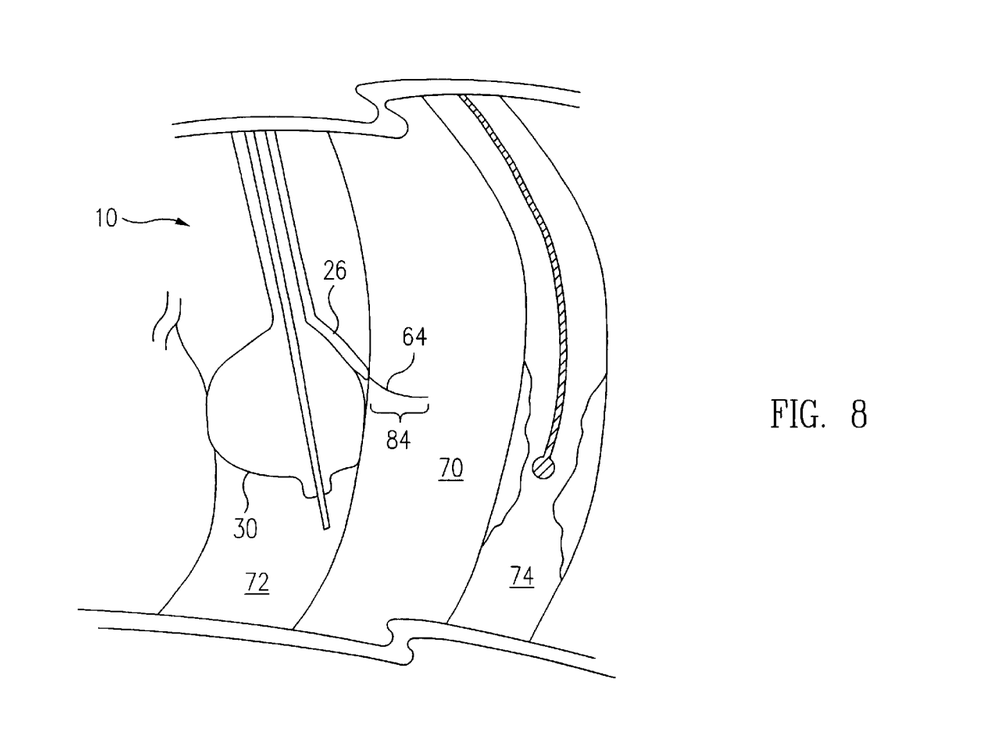
FIG. 8 illustrates an alternate embodiment of the image of the lumen and device of FIG. 4.

Additionally, since the size of the catheter 10 and its components are known, accurate calculations and measurements can be made of the structures within the lumen. When the needle. 64 is optimally positioned at the target site 70, the balloon 30 is inflated with fluid. As shown in FIGS. 7 and 8, in one embodiment, the ultrasonic element 38 of the main body portion 18 and hollow sphere 68 of the secondary body portion 20 are positioned in two distinct lumens separated by tissue. The inflated balloon 30 securely situates the catheter 10, and thereby the needle 64, within the lumen. The inflated balloon 30 also prevents the catheter 10 from sliding out of position when the needle 64 is inserted into the tissue between the two lumens. In general, as the needle 64 is advanced out of the needle lumen 26 and contacts the tissue surface, the resistance of the tissue to needle penetration has a tendency to force the needle 64 and associated catheter 10 in a direction approximately opposite to the direction of needle advancement/penetration. However, the friction between the balloon 30 and tissue surfaces prevents movement of the catheter 10, thereby forcing the tip of the needle 64 into the tissue. As shown in FIG. 8, the depth of needle penetration 84 can be easily calculated using the ultrasonic image. As such, the needle 64 can be extended a predetermined depth into the tissue and/or target site 70. This allows accurate delivery of, for example, drug to the target area 70 (i.e. in one embodiment, the tissue located between the two lumens) and, thus, enhanced treatment capabilities.

After the desired amount of drug is delivered to the target site 70, the needle 64 is retracted and removed from the tissue. The fluid is also removed from the balloon 30 so that the balloon 30 returns to its low profile, deflated state. At this point, the device 10 may be repositioned at ail alternate target site 70 for additional drug delivery according to the above-described procedure. Alternatively, upon completion of the procedure, the device 10 may simply be removed from the lumen of the patient.

By imaging the target area and associated structures, a user of the device 10 is able to precisely identify the desired injection site. As previously explained, angiogenesis, restenotic drug therapies and other related procedures require injections of various fluids including, but not limited to, therapeutic agents, diagnostic reagents, and genetic material, whereby the fluids are delivered directly to the diseased target area. Ultrasonic imaging enables device users to track needle movement, location and depth of penetration into tissue.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A device for delivering a drug directly to a target site comprising:
   an elongated tubular main body portion having a distal end and a proximal end, said main body portion housing:
      a retractable ultrasound component having a transducer, said transducer located near a distal end of said retractable ultrasound component;
      a guide wire lumen configured to slidably receive a primary-guide wire therein;
      a drug delivery element;
      at least one fluid lumen; and
      a balloon attached near said distal end of said main body portion and in fluid communication with said at least one fluid lumen; and
   a flexible, secondary body portion including a secondary-guide wire, said secondary body portion having a proximal end and an ultrasound component located at a distal end of said secondary body portion, wherein said ultrasound components of said main body portion and said secondary body portion are in signal communication, and
   wherein said retractable ultrasound component of said main body portion is capable of being moved within said main body portion so that the position of said retractable ultrasound component can be adjusted relative to the position of said ultrasound component of said secondary body portion.

2. The device of claim 1 further comprising:
   an intravascular ultrasound system connected to said ultrasound components of said secondary body portion and said main body portion.

3. The device of claim 1, wherein said drug delivery element comprises a needle lumen having a needle housed therein, said needle extendable from said lumen to said target site and configured to deliver a drug to said target site.

4. The device of claim 1 wherein said transducer is an ultrasound transducer.

5. The device of claim 1 wherein said transducer is a transducer array.

6. A medical system comprising:
   a first body portion for inserting in a body lumen, said first body portion housing a retractable ultrasonic element; and
   a second body portion for inserting in a body lumen, said second body portion including an ultrasonic element, wherein said ultrasonic elements of said first and second body portions are in signal communication,
   wherein said first body portion includes a drug delivery member, said drug delivery member being extendable out from said first body portion, and wherein said ultrasonic element of said first body portion is adjustable within said first body portion relative to said ultrasonic element of said second body portion and said drug delivery member so that said ultrasonic elements of said first body portion and said second body portion can determine the location of said drug delivery member relative to said first body portion when said drug delivery member is extended out from said first body portion.

7. The system of claim 6, wherein said ultrasonic element of said secondary body portion is configured as a hollow sphere.

* * * * *

UNITED STATES PATENT AND TRADEMARK OFFICE
CERTIFICATE OF CORRECTION

PATENT NO. : 6,645,195 B1  Page 1 of 1
DATED : November 11, 2003
INVENTOR(S) : Vinayak D. Bhat et al.

It is certified that error appears in the above-identified patent and that said Letters Patent is hereby corrected as shown below:

Column 1,
Line 45, change "combinations thereof used to treat" to -- combinations thereof, used to treat --.

Column 2,
Line 23, change "lipids are fonned" to -- lipids are formed --.

Column 5,
Line 58, change "ultrasonic velds" to -- ultrasonic welds --.

Column 9,
Line 13, change "needle. 64" to -- needle 64 --.

Signed and Sealed this

Thirteenth Day of January, 2004

JON W. DUDAS
*Acting Director of the United States Patent and Trademark Office*